(12) United States Patent
Spears

(10) Patent No.: US 6,486,678 B1
(45) Date of Patent: Nov. 26, 2002

(54) METHOD FOR NON-DESTRUCTIVE ANALYSIS OF ELECTRICAL POWER SYSTEM EQUIPMENT

(75) Inventor: Paul Spears, 124 S. 3$^{rd}$ St., Jacksboro, TX (US) 76458

(73) Assignee: Paul Spears, Jacksboro, TX (US)

( * ) Notice: Subject to any disclaimer, the term of this patent is extended or adjusted under 35 U.S.C. 154(b) by 0 days.

(21) Appl. No.: 09/724,183

(22) Filed: Nov. 28, 2000

(51) Int. Cl.$^7$ ................................................ G01R 31/00
(52) U.S. Cl. .......................................... 324/555; 73/570
(58) Field of Search ................................ 324/424, 555; 73/570, 769

(56) References Cited

U.S. PATENT DOCUMENTS

| | | | |
|---|---|---|---|
| 4,480,480 A | * 11/1984 | Scott et al. | 73/769 |
| 4,707,687 A | * 11/1987 | Thomas et al. | 340/680 |
| 5,566,092 A | * 10/1996 | Wang et al. | 364/551.2 |
| 5,852,793 A | * 12/1998 | Board et al. | 702/183 |
| 5,995,910 A | * 11/1999 | Discenzo | 702/56 |

* cited by examiner

*Primary Examiner*—N. Le
*Assistant Examiner*—T. R. Sundaram
(74) *Attorney, Agent, or Firm*—David G. Henry

(57) ABSTRACT

The invention is of a method by which operating mechanical components of an electrical power distribution system may be evaluated to determine whether or not they exhibit operational characteristics which indicate sub-standard performance or imminent mechanical failure. Properly operating machines will produce "signatures" which are apparent from the measuring and depicting (graphically in most cases) of such parameters as decibel production over time, sound production in terms of frequency over time, and amplitude sound at different frequencies over time. A mechanical device which is malfunctioning to a greater than nominal degree will produce such signatures as are recognizably, and, in most cases, perceptively different through mere visual examination and comparison with normal signatures.

1 Claim, 23 Drawing Sheets

PROCESSING SETTINGS

Frequency Range and Resolution

Sampling Rate (Hz): 48000
Decimation Ratio: 1
FFT size (samples): 4096
Spectral Line Resolution: 11.719 Hz
Frequency Limit: 24000.000 Hz

Sampling Format
- ○ 8 bit
- ● 16 bit
- ● Mono (left)
- ○ Sterio

Averaging Settings

3

☐ Peak Hold

- ● Exponential
- ○ Linear
- ○ Vector

FFT Overlap (Post Processing Mode only)

Percentage: 0
Time Resolution: 85.33 (msecs)

Smoothing Window

Blackman

Dual Channel Spectral Processing Options (Stereo Mode only)

Left channel only

Delay Channel: ○ Right  ● Left
Delay Time (msec): 0.000

Input Signal Overload

☑ Enable Overload Detection  ☐ Exclude Overloaded Data From Processor

[Ok] [Cancel] [Defaults] [Help]

*Fig. 7*

METHOD FOR NON-DESTRUCTIVE ANALYSIS OF ELECTRICAL POWER SYSTEM EQUIPMENT

BACKGROUND OF THE INVENTION

1. Field of the Invention

The present invention relates to testing methods for evaluation the operation of mechanical devices through acoustical recording and analysis.

2. Background Information

Maintenance of an electrical distribution system is extraordinarily expensive for utilities, and failures in such a system can be equally, if not more expensive, in the aggregate for utility customers (loss of computer data, food spoilage, work interruptions, loss of ability to transact with customers, etc.). It is clear, then, that preventative maintenance, if feasible, is highly desirable. However, presently known and implemented technology and methods do not economically allow the preemptive detection of problems which account for the majority of power interruptions in an electricity distribution system.

Over 80% of all power interruptions in an electrical power distribution system are caused at the power substation level (as opposed to downed peripheral lines and lightening strikes, for example). Of the substation malfunctions which cause power interruptions, over 40% are caused by malfunctioning mechanical electrical power system components. At present, power companies seldom know of a malfunctioning switch, breaker, load tap charger ("LTC"), or motor until it fails and a real power interruption has already occurred. Present skill and methods in the field do not provide reliable means of otherwise detecting a malfunctioning, or soon-to-be malfunctioning mechanical components, other than tearing them down for physical inspection—a cost prohibitive approach to preventative maintenance. A few non-invasive testing methods are known or proposed (ultrasound imaging, for example), but these are not proven, and have very limited application in terms of the components with which they are even arguably useful.

It would well serve utilities and their customers, to a degree which is, perhaps, impossible to fully value, to provide some means by which the utilities could detect sources of likely substation-level malfunctions of mechanical components in an electrical power system (switches, breakers, LTCs and motors) before they occur in order to minimize the incidences of actual power interruptions.

SUMMARY OF THE INVENTION

It is an object of the present invention to provide a non-destructive testing and evaluation method by which damaged or malfunctioning mechanical components in an electrical power system in an electrical distribution system may be detected in a cost effective and easily carried out method.

It is another object of the present invention to provide a method by which preventative maintenance of mechanical components in an electrical power distribution system may be cost effectively carried out on appropriately targeted units, identified through non-destructive, simple analysis.

It is another object of the present invention to provide a novel and cost effective method for identifying mechanical components in an electrical power distribution system which are likely to require imminent repair to prevent failure.

In satisfaction of these and related objects, the present invention provides a remarkably simple and cost effective method by which operating mechanical components of an electrical power distribution system may be evaluated to determine whether or not they exhibit operational characteristics which indicate sub-standard performance or imminent mechanical failure. The present method is based on the fact that mechanical devices produce a mix of sound comprised of the individual sounds generated by the actions of various components associated with their operations.

Properly operating machines will produce "signatures" which are apparent from the measuring and depicting (graphically in most cases) of such parameters as decibel production over time (relative amplitude expressed in dB), sound production in terms of frequency over time, and relative amplitude sound at different frequencies over time. A mechanical device which is malfunctioning to a greater than nominal degree will produce such signatures as are recognizably, and, in most cases, perceptively different through mere visual examination and comparison with normal signatures. Even when reference signatures of properly operating mechanical devices are not available, a familiarity with devices in certain families of such devices will often allow an experienced technician to recognize likely malfunctioning components (as has been discovered by the present inventor in his work with electrical power system equipment).

Initial testing and evaluation of the present method has proven remarkably reliable in detecting problems with electrical distribution system switches, breakers, LTC and motors—problems for detecting which a physical tear down was the only clearly reliable alternative. In every case during tests of the present method (several dozen instances) in which the present inventor has identified a suspect breaker or switching unit through practice of the present invention, physical inspection by the utility revealed conditions which unarguably would have soon resulted in failure of the unit and an actual power interruption in the grid.

If implemented on a nationwide basis, the present method can save utilities millions of dollars by avoiding the more costly repairs as attend a total failure of a unit, and by avoiding needless intervention in units which may be deemed "healthy" through use of the method. The savings to utility customers for lack of actual power interruptions will be substantial as well, not to mention the enhanced, over-all safety arising from fewer power losses to medical facilities, traffic lights, etc.

BRIEF DESCRIPTION OF THE DRAWINGS

FIG. 7 shows the Process Settings control window of the preferred software useful for sound data processing in the present method.

DETAILED DESCRIPTION OF THE PREFERRED EMBODIMENT

The present method for non-destructively evaluating mechanical devices for damages or somehow misaligned components is based on the premise that the vibrations of operating machines are identifiable as graphically depictable "signatures" according to parameters of relative energy levels in dB over time, frequencies of energy produced over time, and relative amplitude/energy decibel production at specific frequencies over time. The present inventor has discovered that a mechanical device which is malfunctioning to a greater than nominal degree will produce such signatures which are recognizably different from the signatures of properly operating equipment of like construction through mere visual examination. These principles have proven reliable and very useful in the present inventor's testing and fine-tuning of his invention in actual field trials.

The principle embodied here is that a fundamental wave is derived of the summation of a number of higher frequencies out to the nth degree such that the frequencies higher than N are basically insignificant. This, by definition, allows that the total energy can be dispersed in a summation of frequencies derived from the fundamental wave. It then becomes apparent that there are basically an infinite number of possible combinations. This is the key—most machines will produce similar frequency energy levels if operating properly.

Figure 1A:
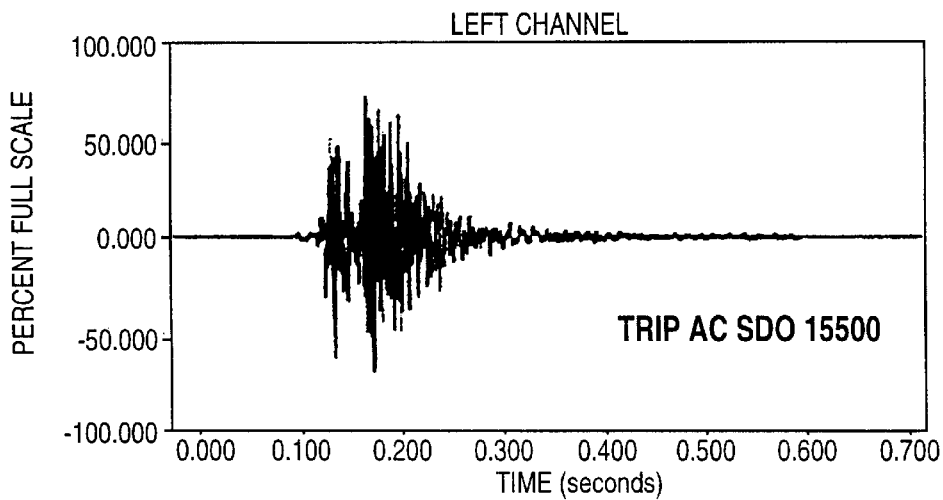
FIG. 1 depicts three example displays of the decibel signatures (decibels [relative amplitude expressed in dB] vs. time) of three low voltage circuit breakers. This is, in effect, a depiction of the total energy produced by the event over time.
Figure 1B:
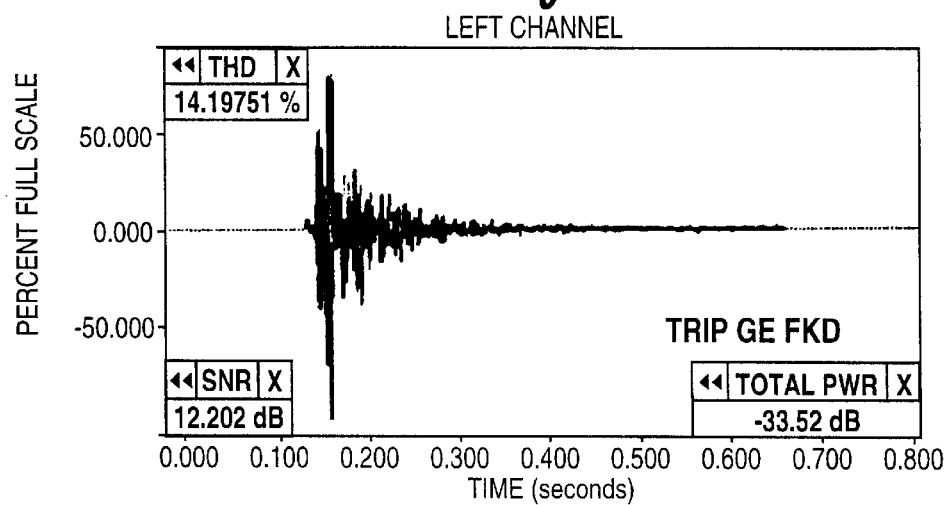
Figure 1C:
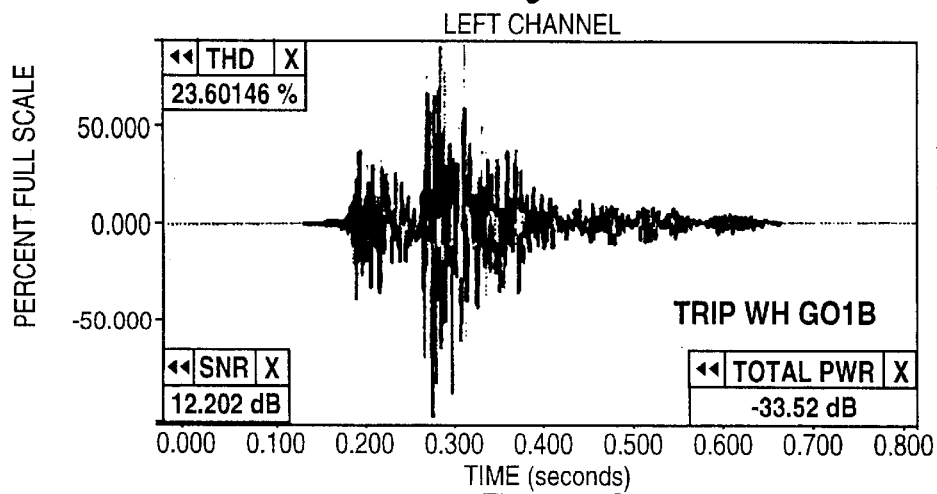
Figure 2B:
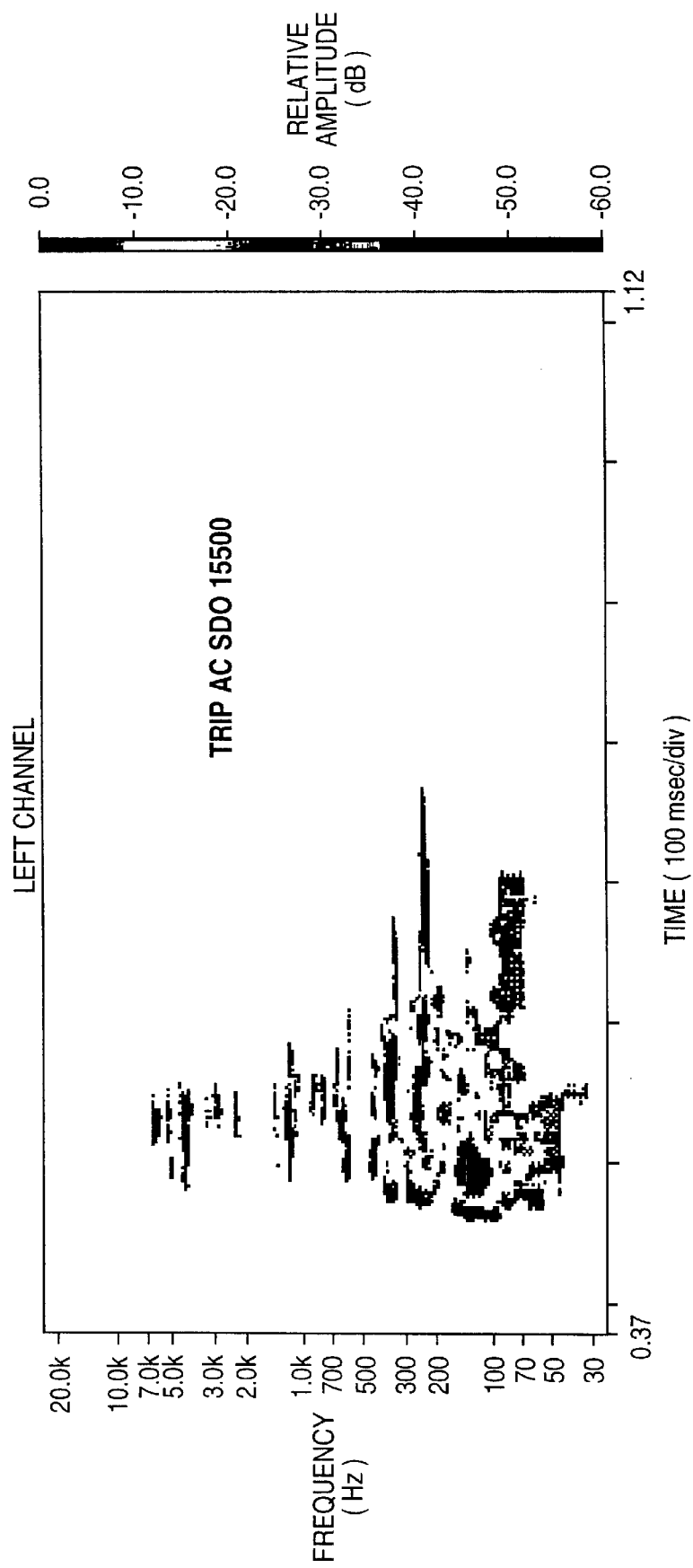
FIG. 2 depicts the signatures of the same units as referenced in FIG. 1, when depicted as a graphic display of the frequency of vibrations emanating from the units over time (with shading indicating the amplitude of vibrations over the frequencies spectrum).
Figure 2B:
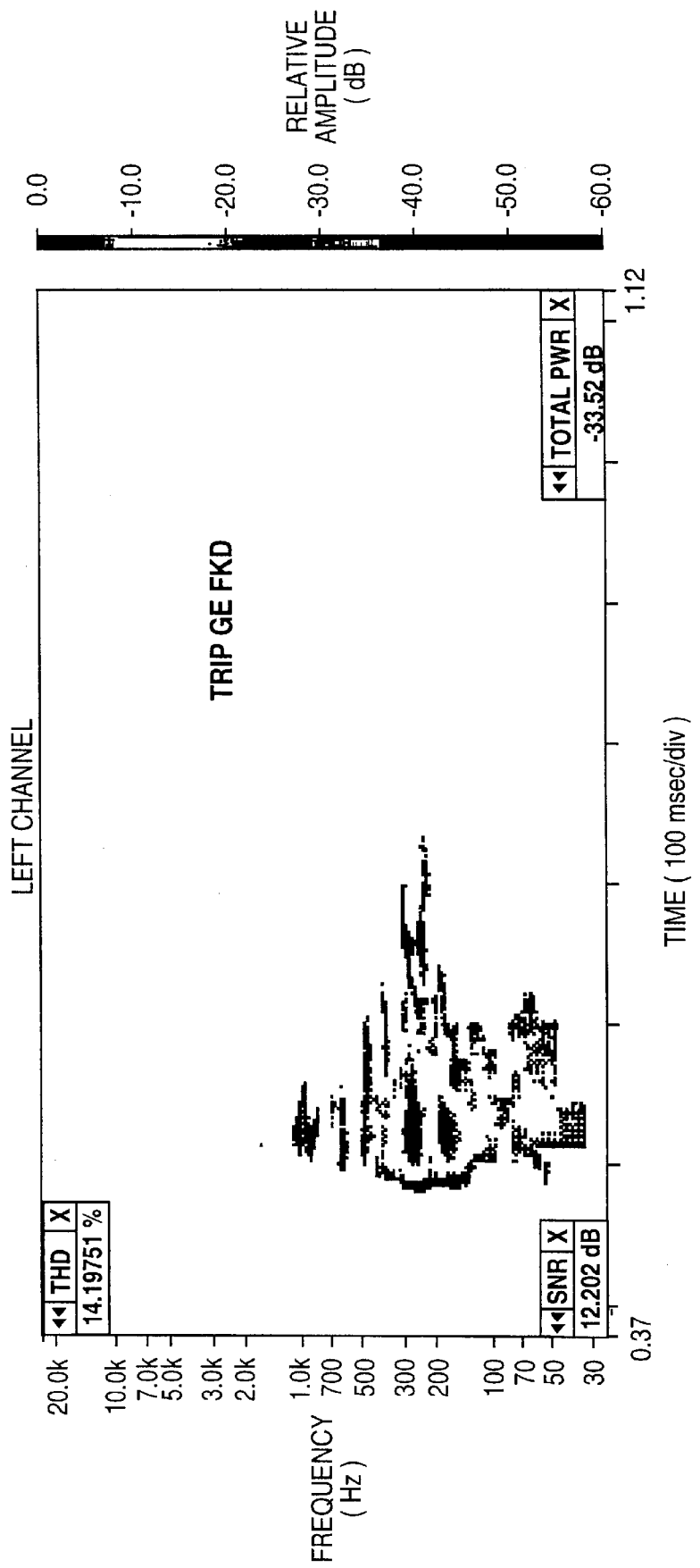
Figure 2C:
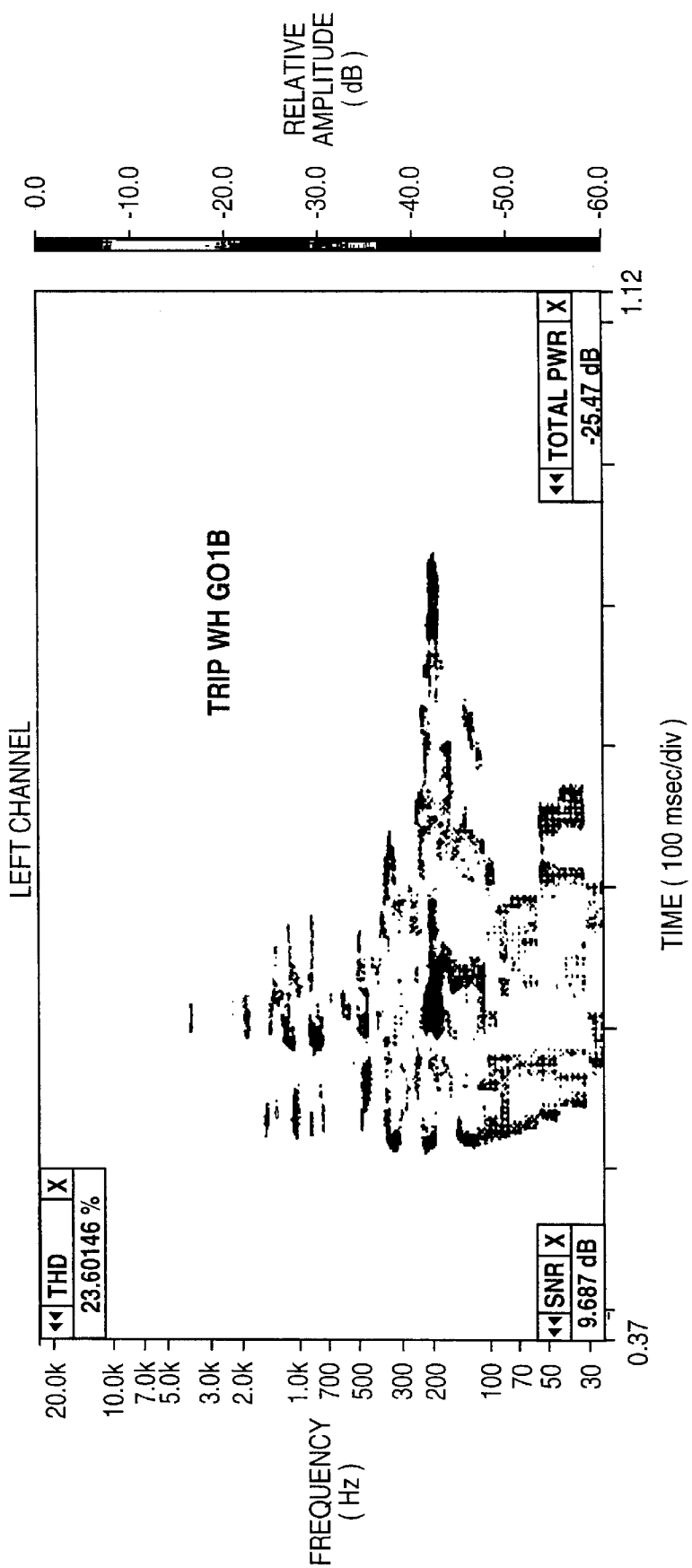
Figure 3A:
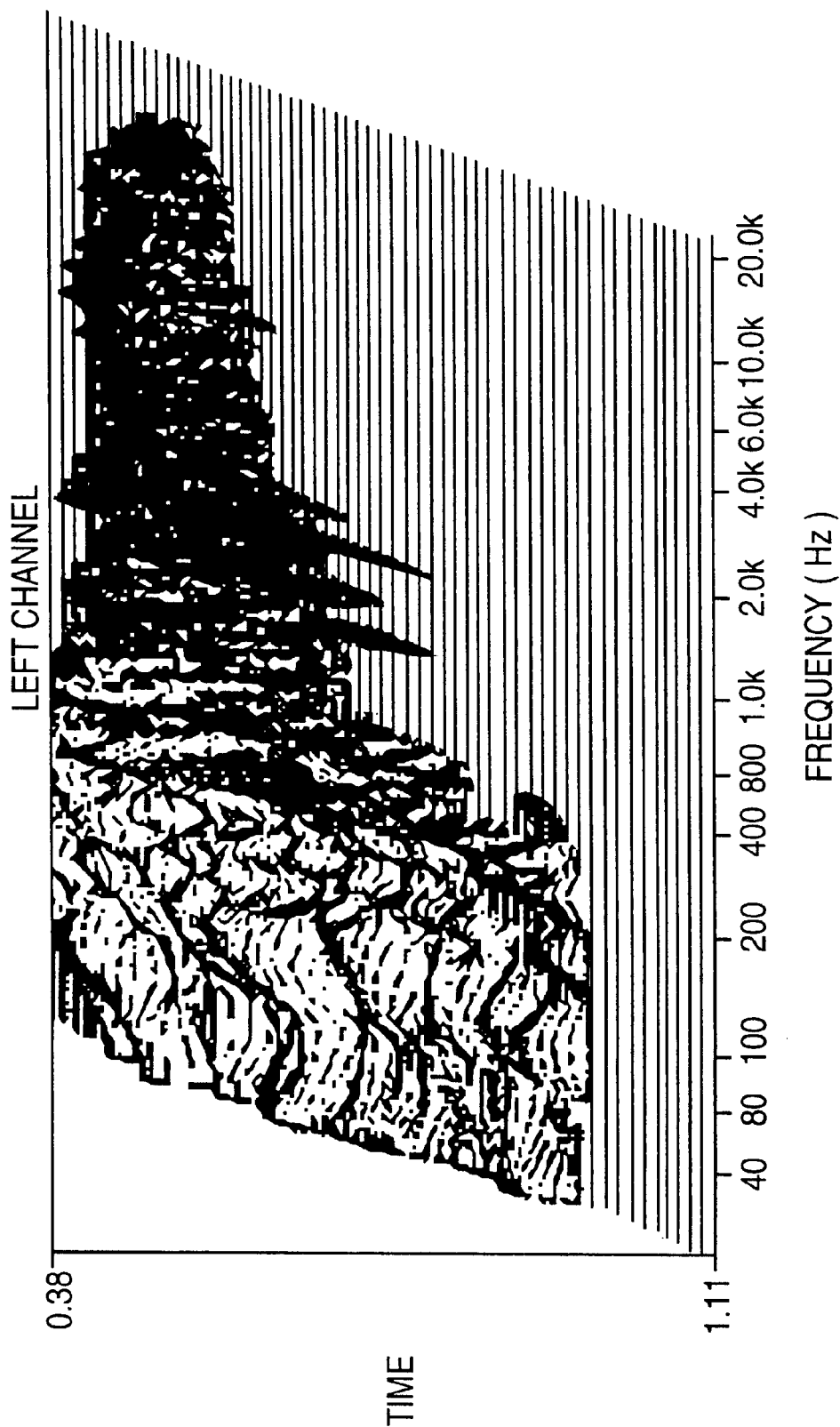
FIG. 3 shows a three dimensional graph of the vibrations of a mechanical device with the x-axis representing frequency, the y-axis representing time, and the z-axis representing amplitude.
Figure 3B:
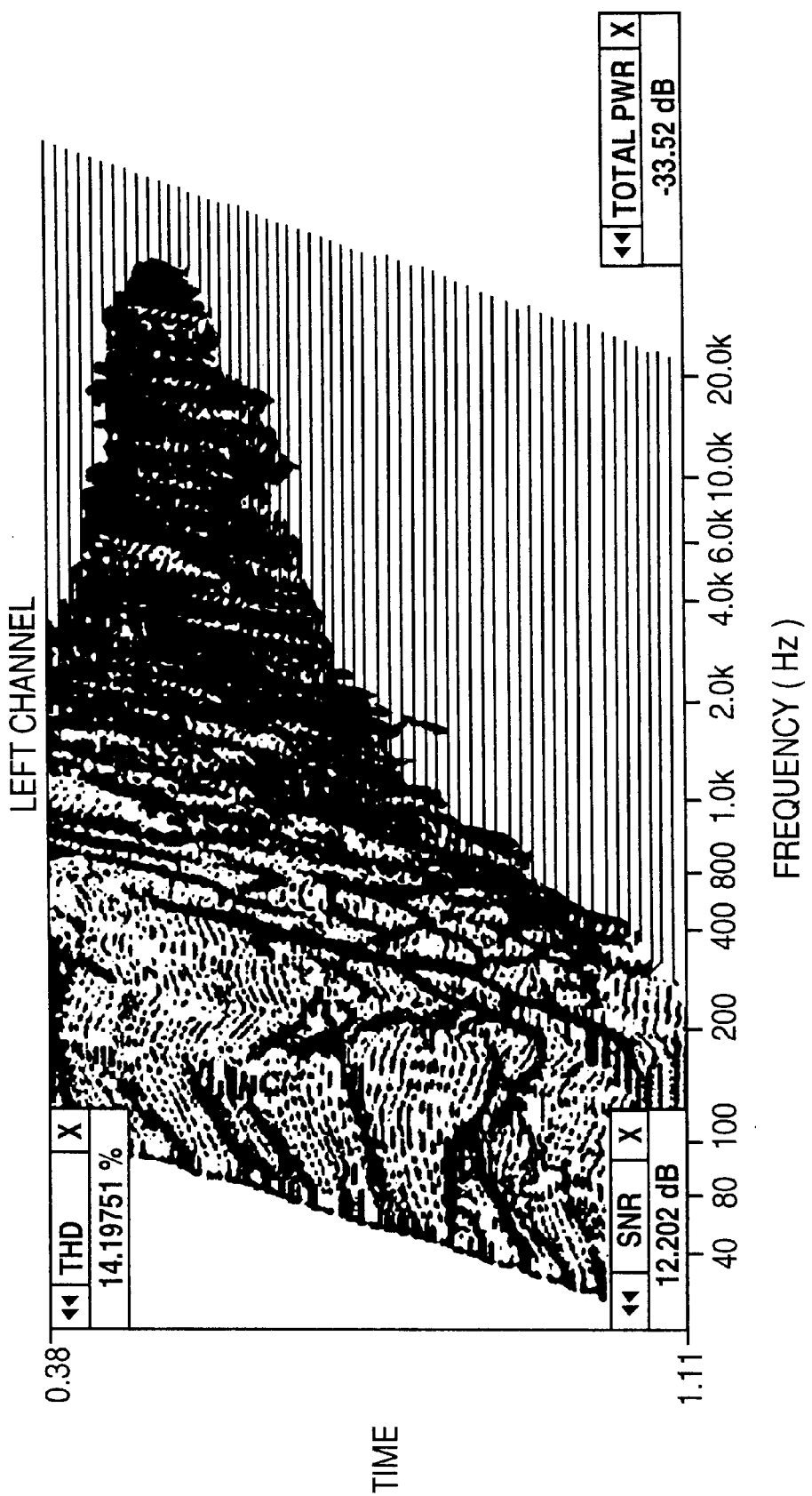
Figure 3C:
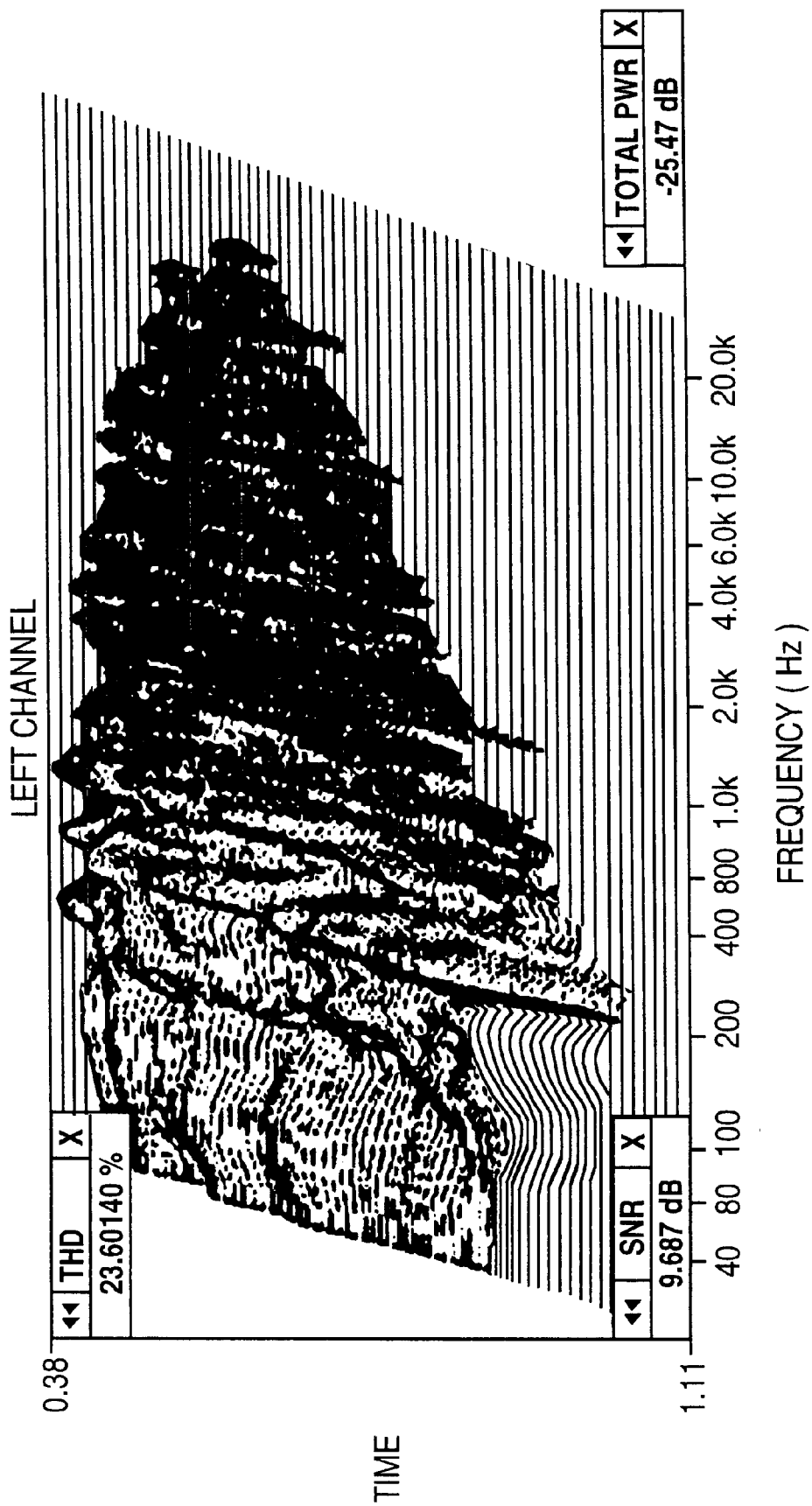

Three example displays of the decibel signatures (decibels vs. time) of three low voltage circuit breakers are shown in FIG. 1. As will be discussed later, these signatures are of normally operating units and are readily distinguished by mere visual examination from like signatures of malfunctioning, like units. FIG. 2 depicts the signatures of the same units when depicted as a graph of the energy levels of the frequency of vibrations emanating from the units over time (with shading optionally indicating the amplitude of vibrations over the frequencies spectrum). FIG. 3 shows a three dimensional graph of the vibrations of a mechanical device with the x-axis representing frequency, the y-axis representing time, and the z-axis representing amplitude.

Any of the above signatures may independently form a reliable basis for detecting a malfunctioning mechanical device, but comparative analysis of reference and field signatures according to all three depiction schemes has proven almost flawless in detecting actual, mechanical defects in electrical distribution system mechanical components.

Detecting and recording the data for graphical analysis (whether for generating a reference data set and related graphical displays, or for field testing of non-reference equipment units) is very simple. According to the presently envisioned best mode of the present invention, a practitioner evaluating electrical distribution system switches, breakers, etc. should use a digital audio tape recorder with suitable microphones attached for detecting the vibrations of the operating equipment. The microphones are placed based on a basic knowledge of the structure of the equipment being analyzed, with the objective being to position the microphone for more closely juxtaposing the internal, mechanical components which are likely to fail. Ideal placement for any given make and model of equipment will be determined by those establishing the reference signatures for the specific equipment, and should be conveyed (by operations manuals, for example) to those who will do field testing. This is important because tests should be conducted with microphones placed on the to-be-tested equipment in virtually identical positions to those used when recording for the reference signatures in order to later be comparing "apples to apples."

Dynamic microphones (magnetic) are preferred over condenser type microphones because condenser types are too sensitive for the loud sharp sounds created by breaker operations. At present, SHURE brand, model SM57 microphones are recommended, because they have produced the most useable and reliable data. A TALCUM brand, model DA-P1 digital audio tape recorder has been used to record the data in trials conducted thus far.

Once recorded, sound data is processed and displayed in the above-described modes using commercial sound editing software running on personal computers of sufficient capacity and speed. To date, Pioneer Software's SPECTRA PLUS software package has proven adequate for practicing the present method. Once process with such software, the images may be saved for later visual display and/or printing using readily available graphics or photo management software (ADOBE's PHOTOSHOP, or MICROSOFT'S PICTURE IT! packages, for example).

Figure 4:
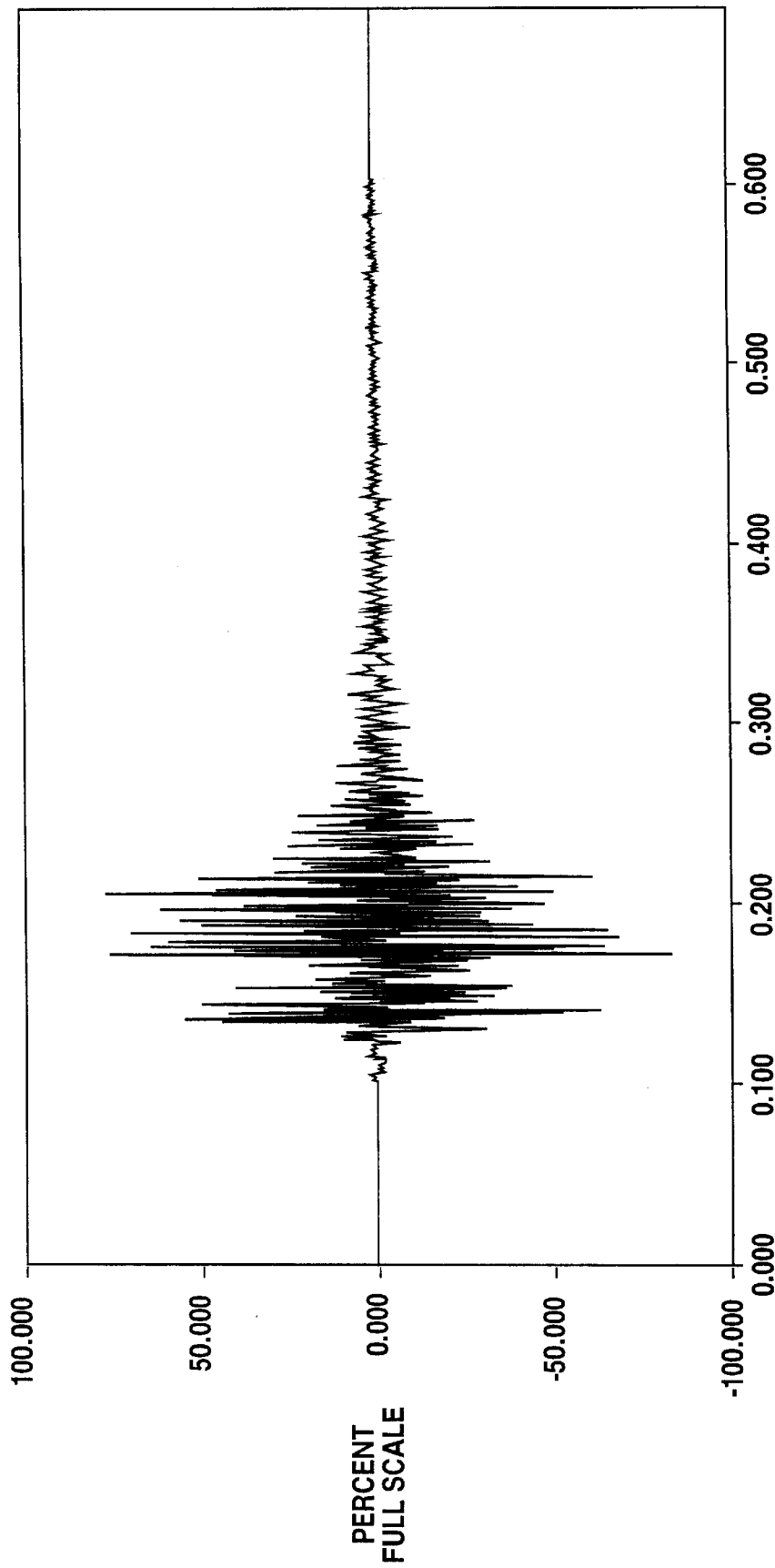
FIG. 4 depicts a real time screen of SPECTRA PLUS is shown depicting the signature of a trip operation of a model AC SDO 15500 breaker according to decibel (relative amplitude expressed in dB) versus time.
Figure 5:
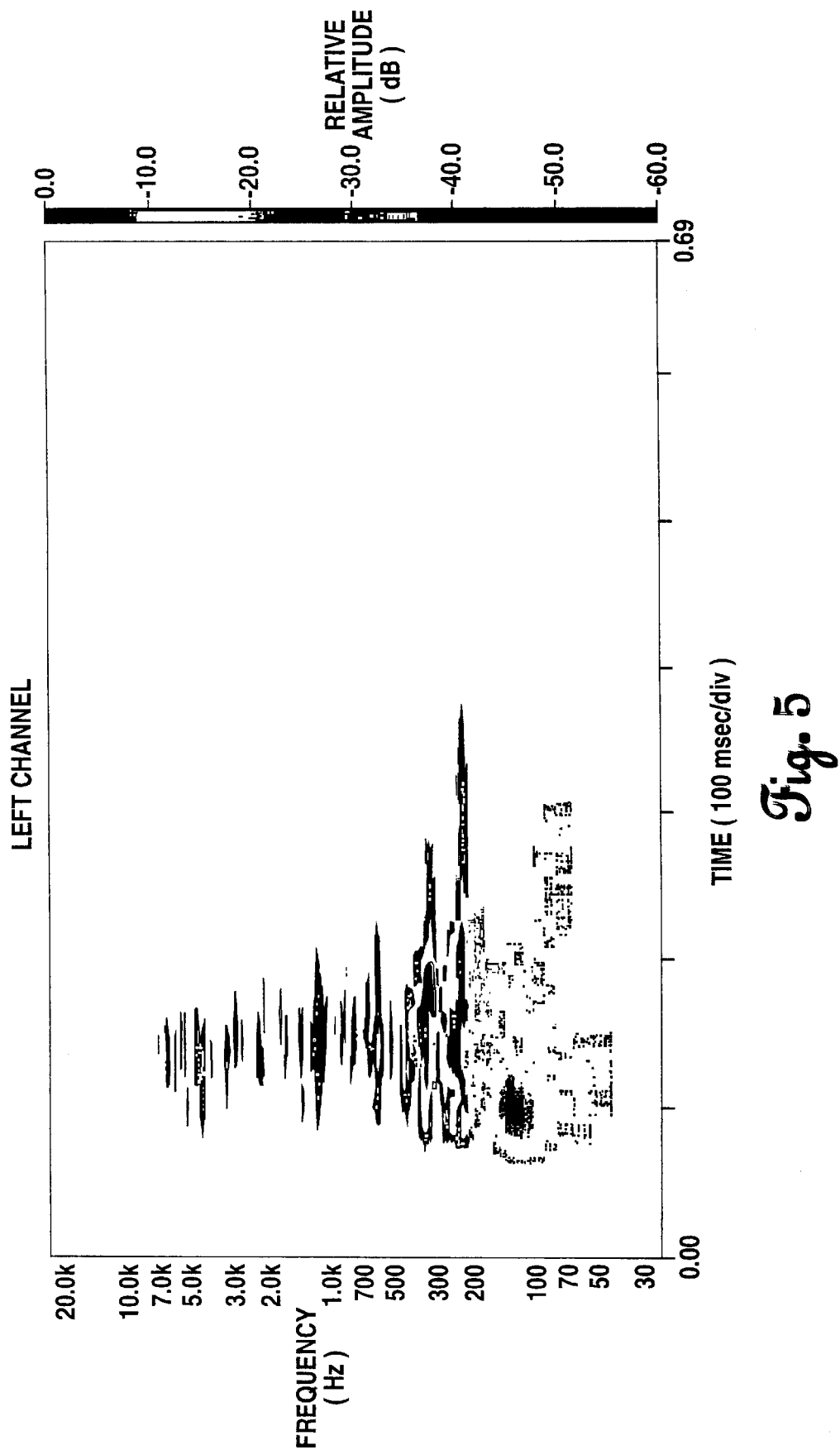
FIG. 5 depicts a spectrum analysis of the same underlying data as in FIG. 4 utilizing a Fast Fourier Transform, whereby the horizontal axis (X) is time, the vertical axis (Y) is frequency and the color (shading in black and white depiction, and scaled on the right side of the window) indicates the relative amount of energy in the frequency spectrums and, for practical definition, can be said to represent the Z-axis of a standard mathematical model.
Figure 6:
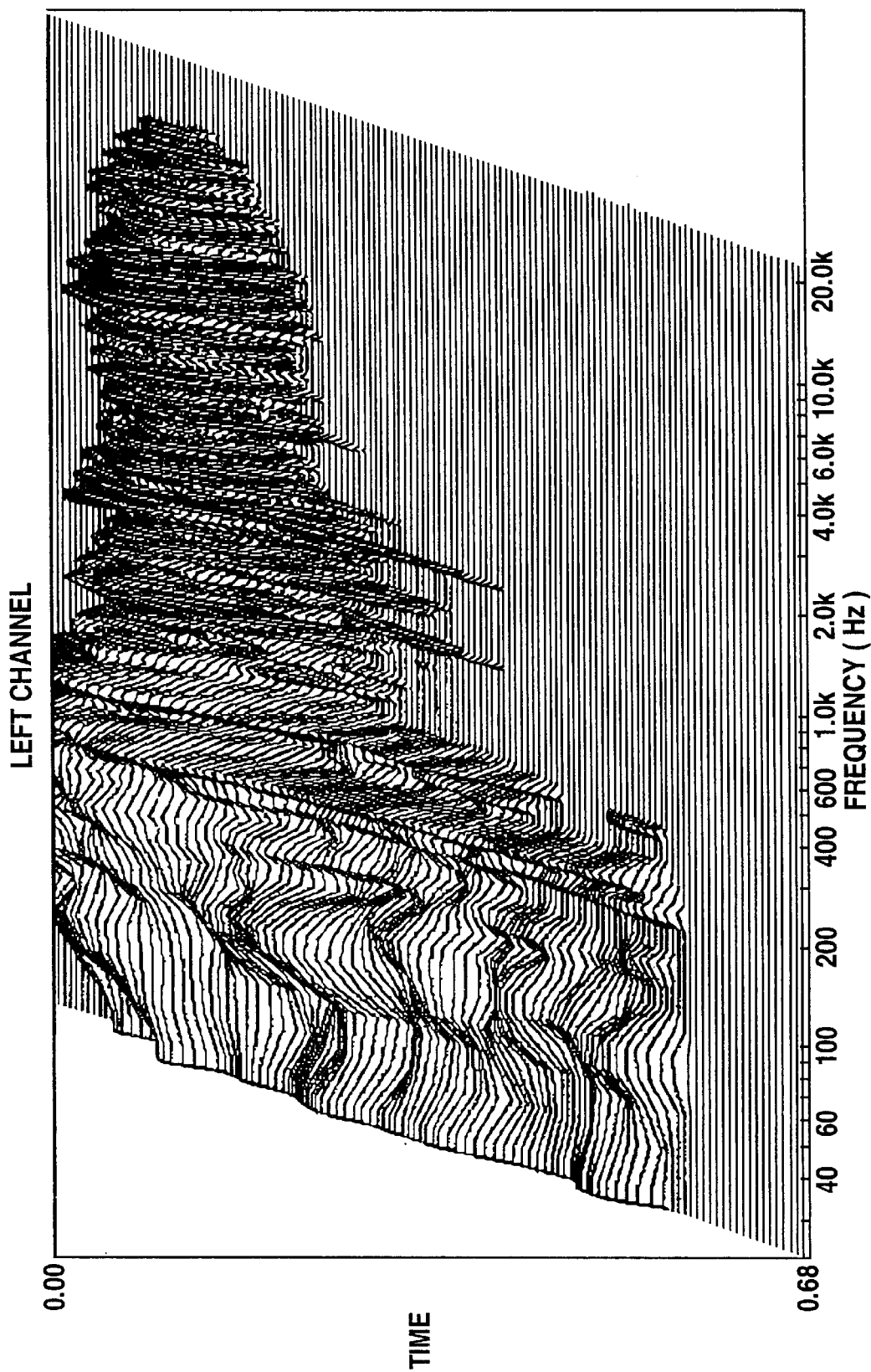
FIG. 6 depicts the same parameters as depicted in FIG. 5 in a three dimensional format.

Referring to FIG. 4, a real time screen of SPECTRA PLUS is shown depicting the signature of a trip operation of a model AC SDO 15500 breaker according to decibel versus time. FIG. 5 depicts a spectrum analysis of the same underlying data utilizing a Fast Fourier Transform, whereby the horizontal axis (X) is time, the vertical axis (Y) is frequency and the color (shading in black and white depiction, and scaled on the right side of the window) indicates the relative amount of energy in the frequency spectrums and, for practical definition, can be said to represent the Z-axis of a standard mathematical model. The same parameters are often, more usefully depicted as a three dimensional model (as described above), such as in FIG. 6.

Figure 8:
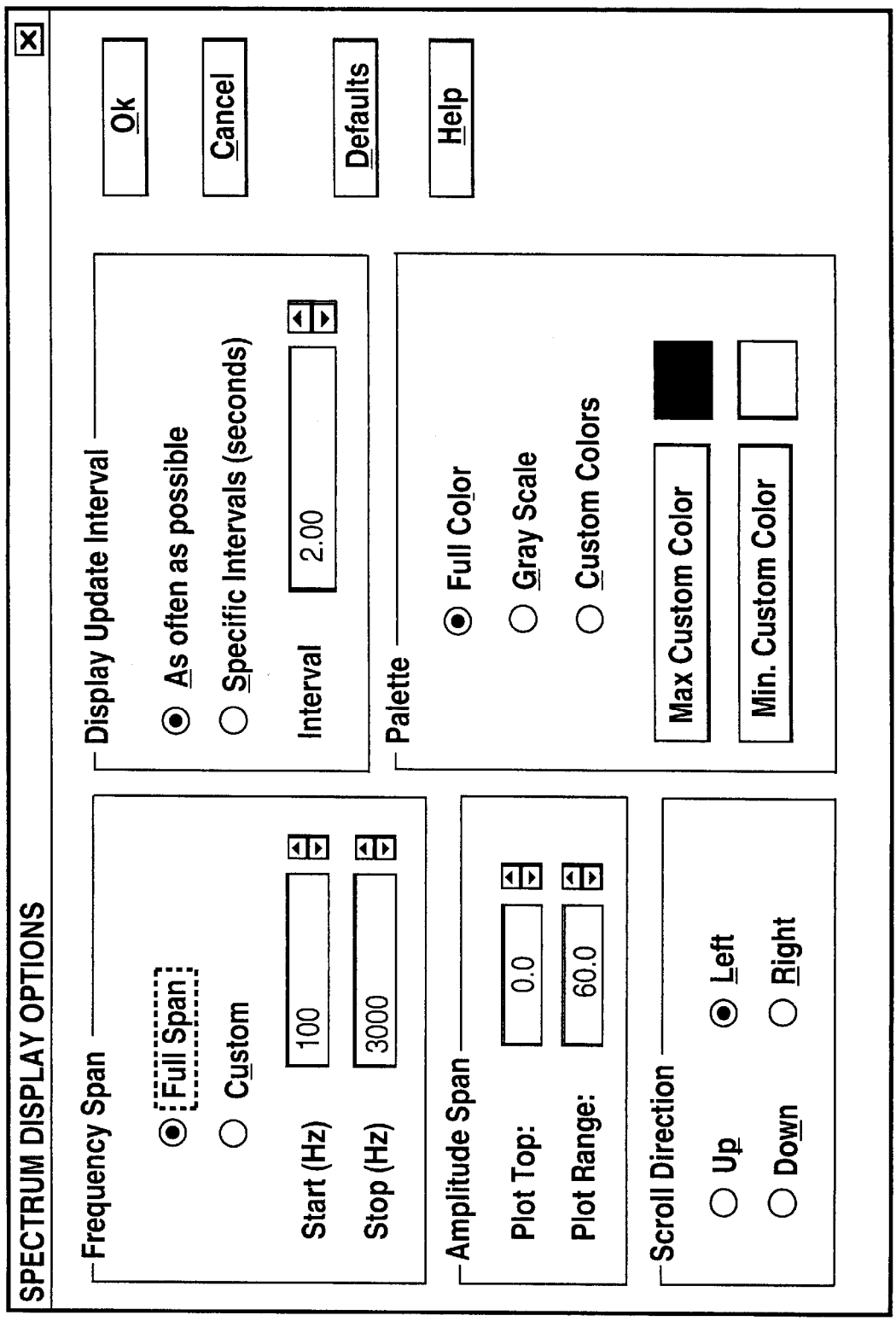
FIG. 8 shows the Spectrogram Display Options control window of the preferred software useful for sound data processing in the present method.

Software settings vary depending on the type of machine being tested such as circuit breakers, transformer load tap chargers ("LTC's") or pumps. Settings may also need to be adjusted even with different manufacture and model of the same type of machine. The main consideration is to determine the optimum combination of settings to achieve the best image while keeping random noise to a minimum, and very limited experience is needed to recognize proper settings for any given application. Consideration must be given to variables such as scaling, FFT sampling size, sampling rate and smoothing window choice. Plot top and range settings are also important. FIGS. 7 and 8 show control windows for these adjustments when using the SPECTRUM PLUS software package.

Once sound data is obtained and images are generated according to the above description, analysis is straight forward and will be taught here by way of examples of actual field tests.

Figure 9A:
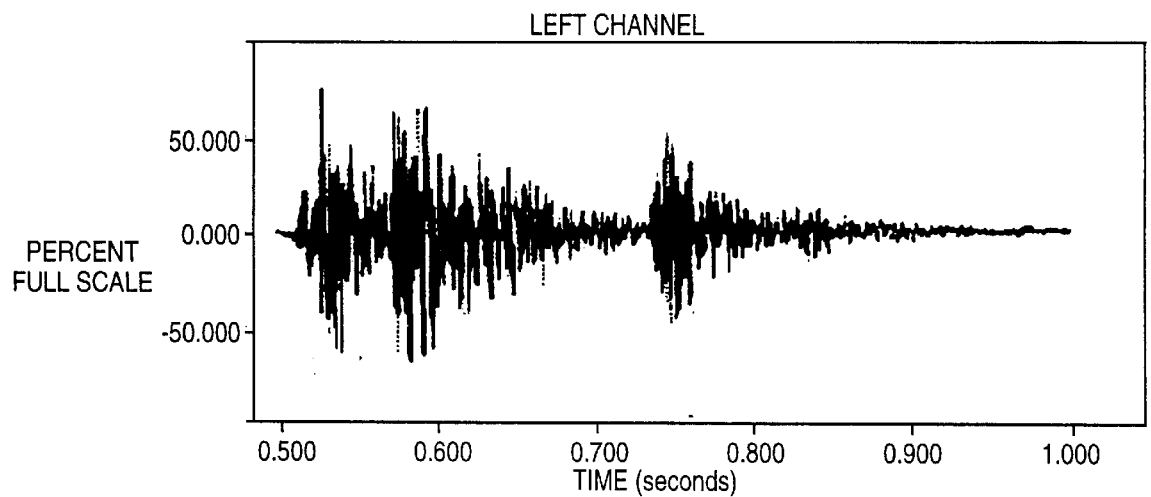
FIG. 9 shows three graphical display modes with respect to a field test of the trip phase of an AC SDO 15500 breaker.
Figure 9B:
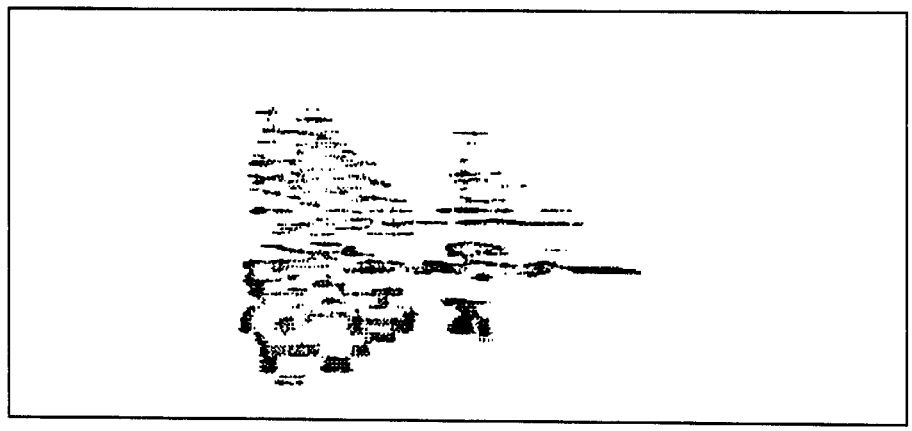
Figure 9C:
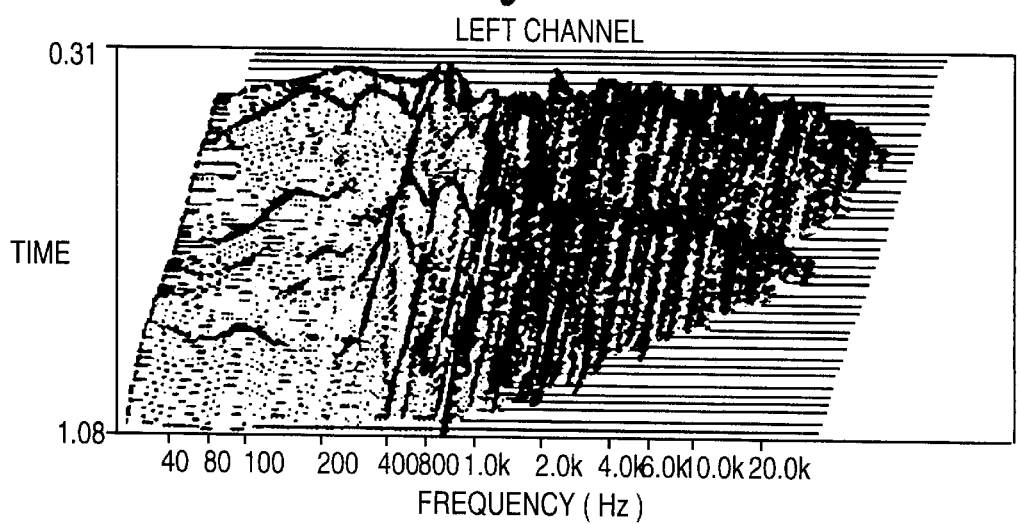
Figure 10A:
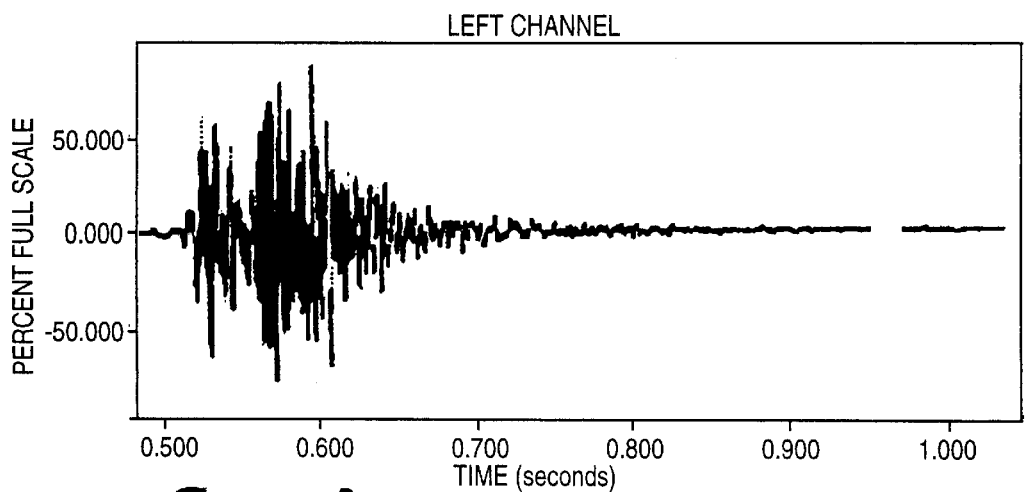
FIG. 10 shows the same three display modes as in FIG. 9 from the trip of a properly operating reference unit.
Figure 10B:
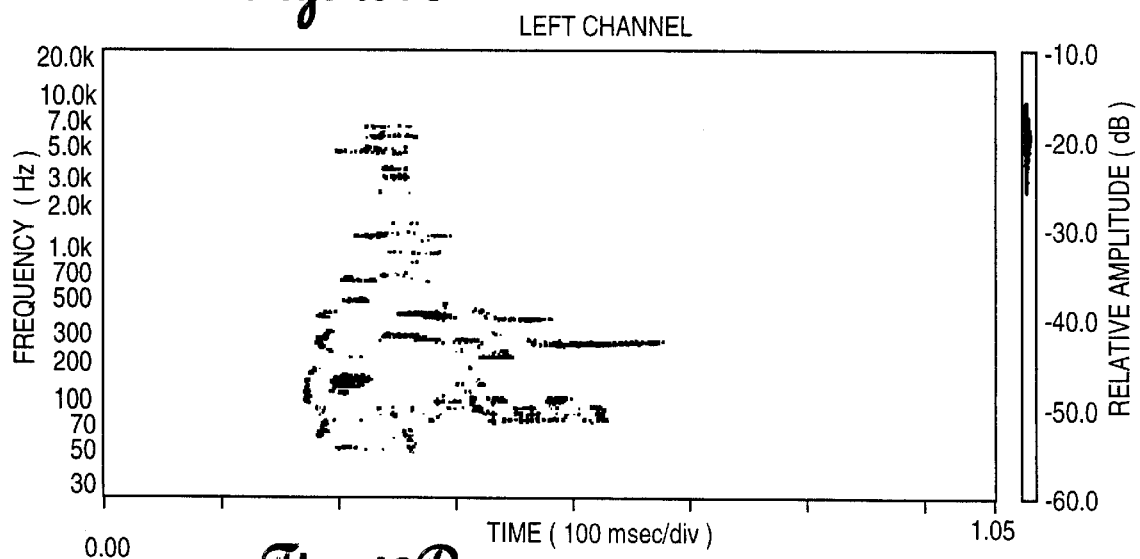
Figure 10C:
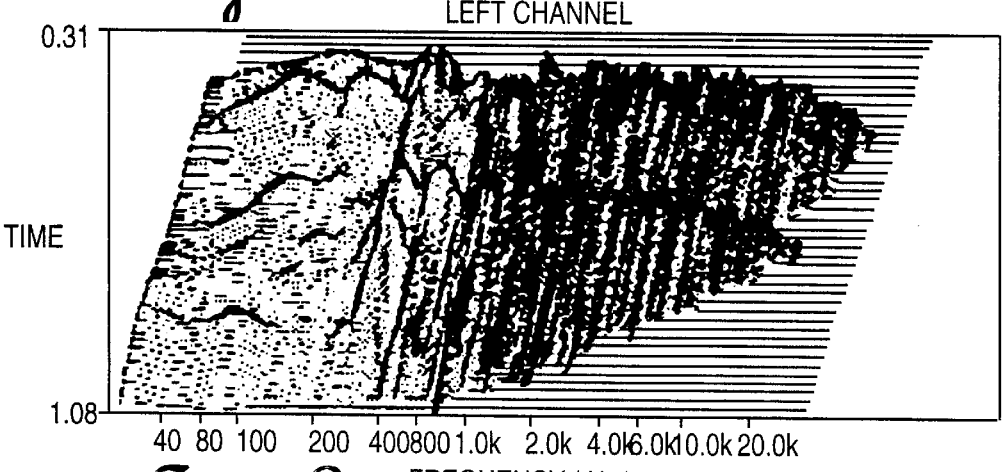
Figure 11A:
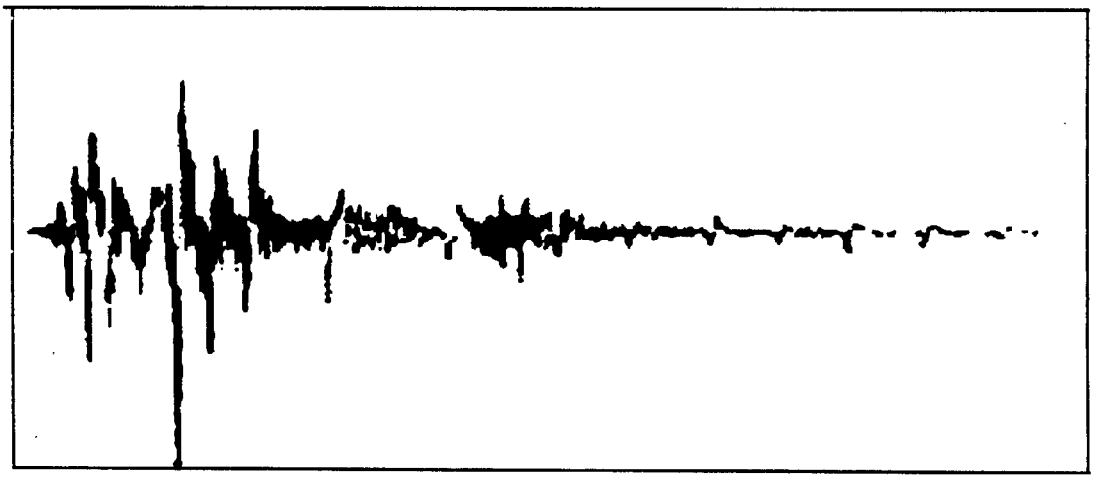
FIG. 11 shows three graphical display modes with respect to a field test of the close phase of an AC SDO 15500 breaker.
Figure 11B:
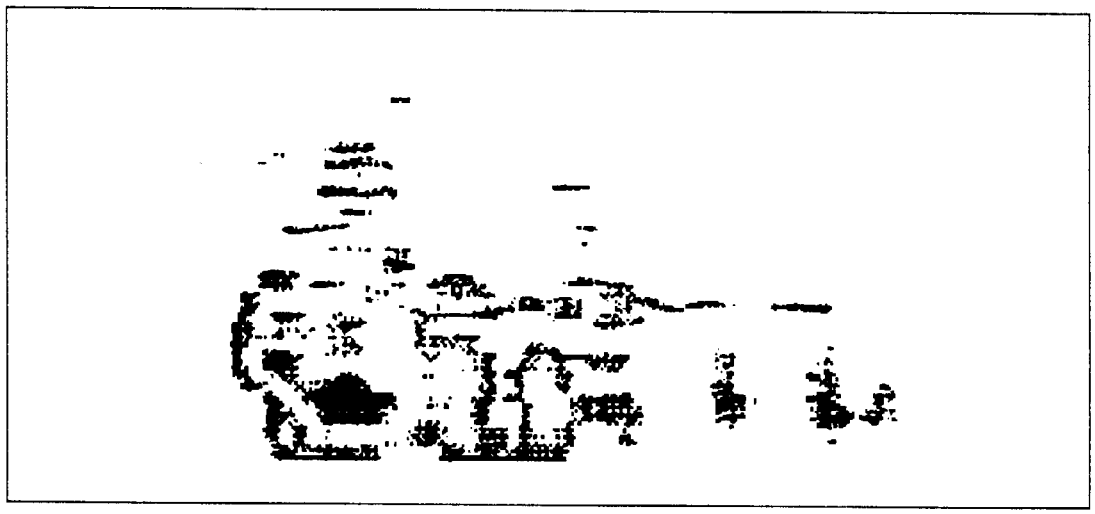
Figure 11C:
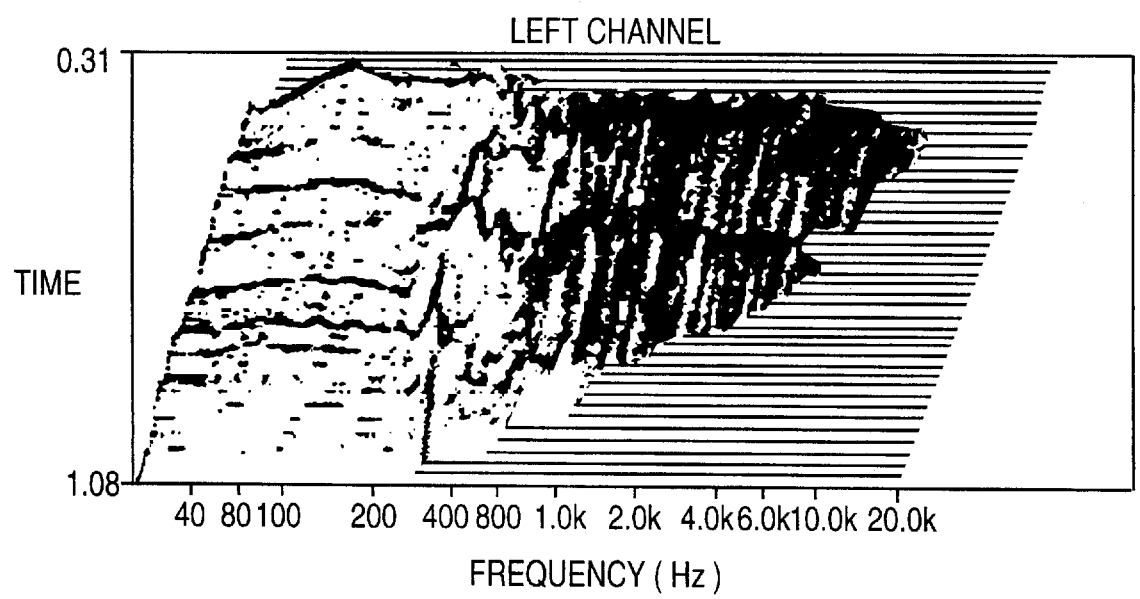
Figure 11D:
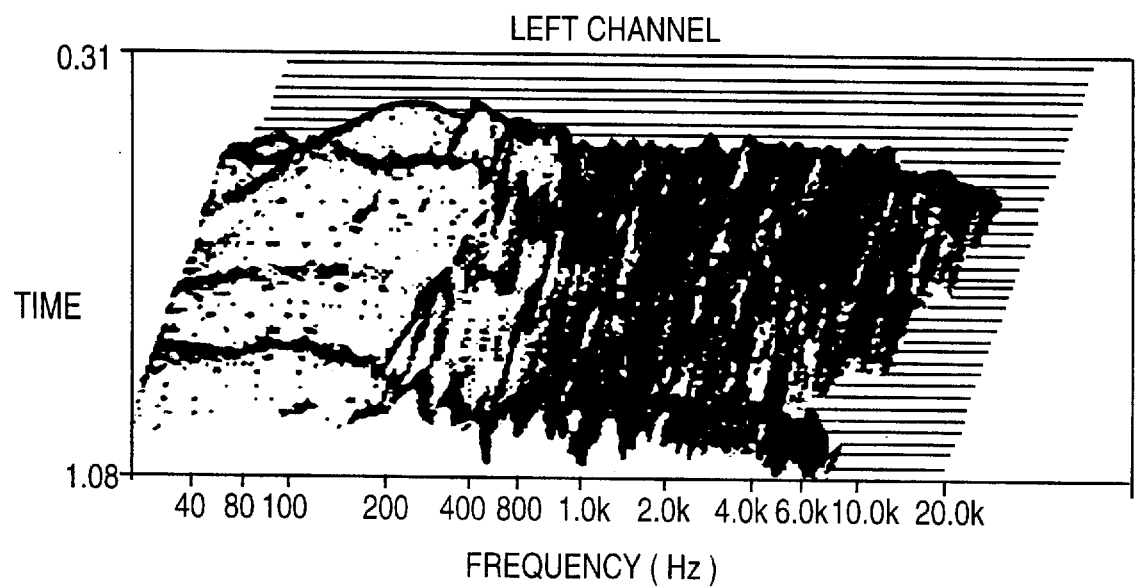
Figure 12A:
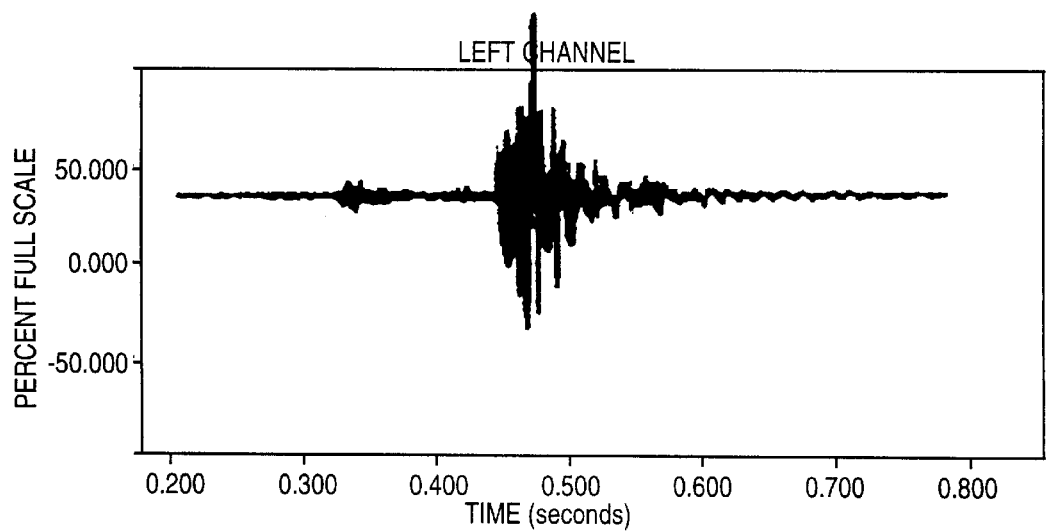
FIG. 12 shows the same three display modes as in FIG. 9 from the close step of a properly operating reference unit.
Figure 12B:
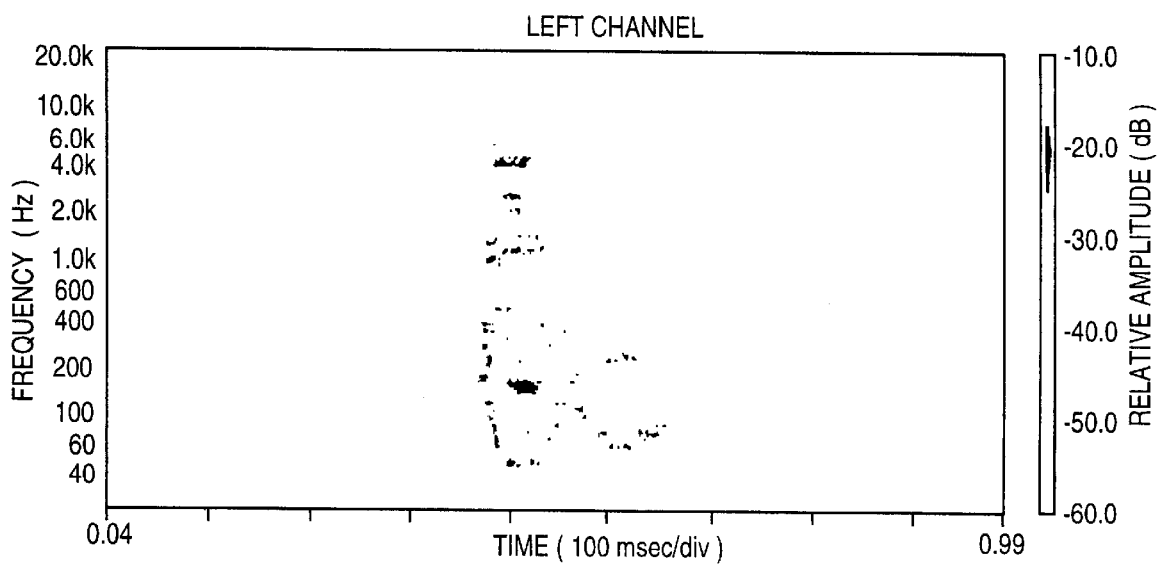
Figure 12C:
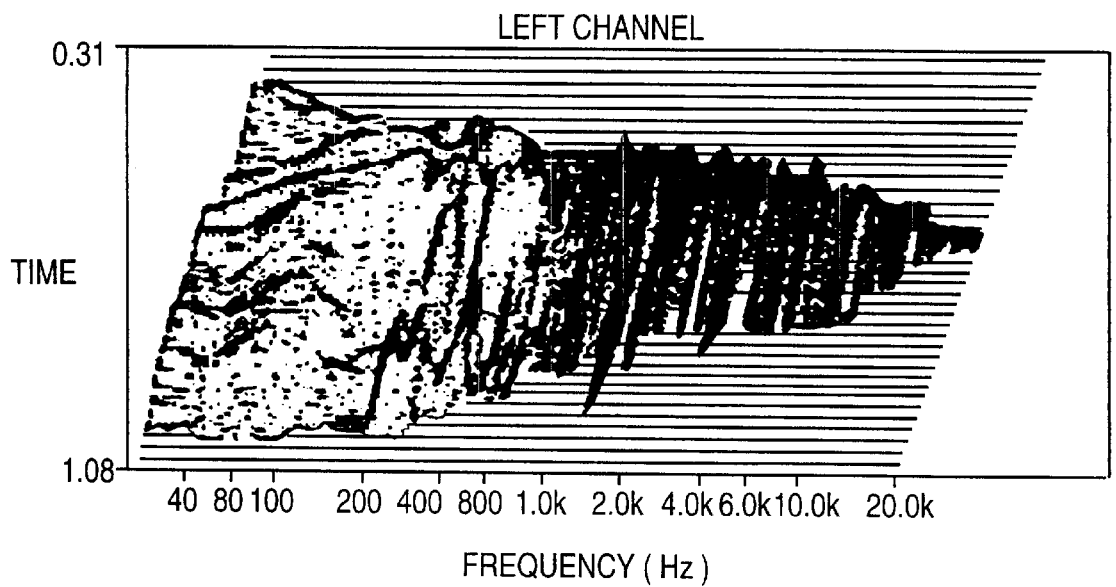
Figure 12D:
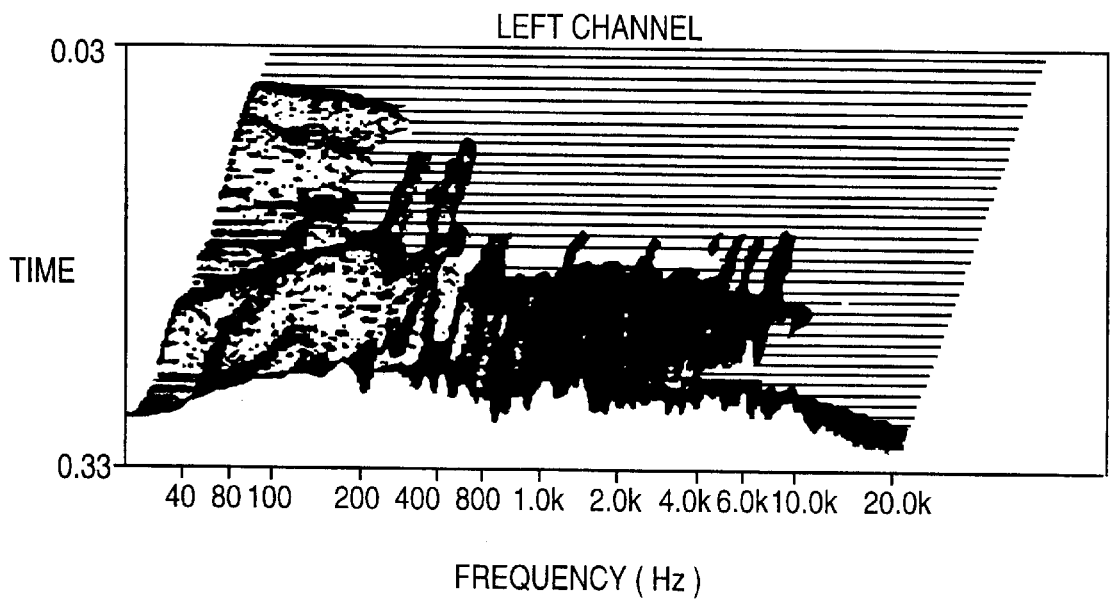
Figure 13A:
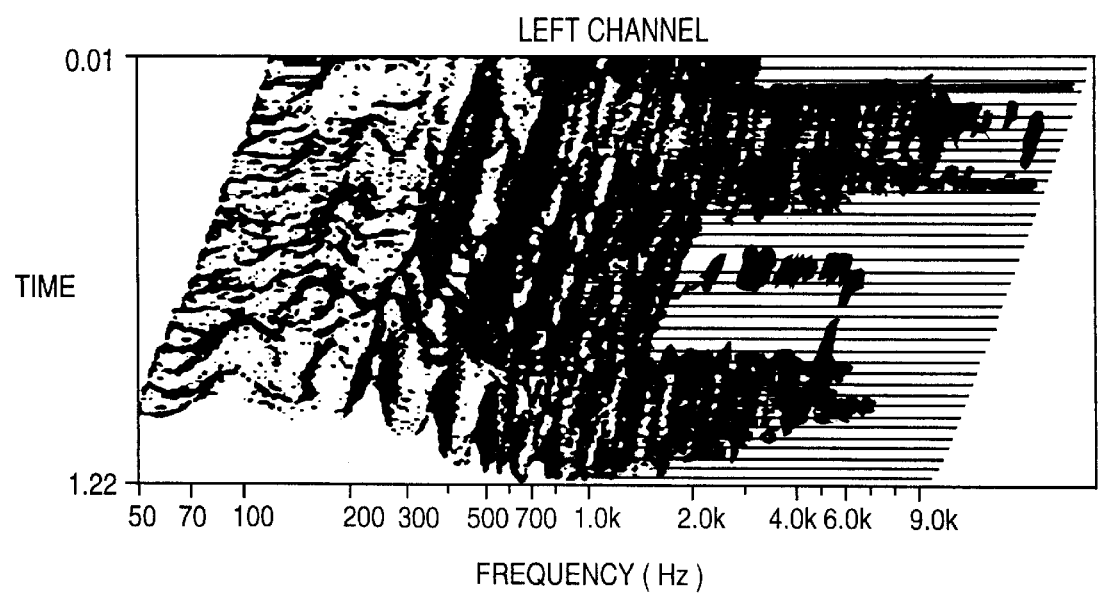
FIG. 13 depicts three dimensional signatures of the trip step of a defective LTC unit.
Figure 13B:
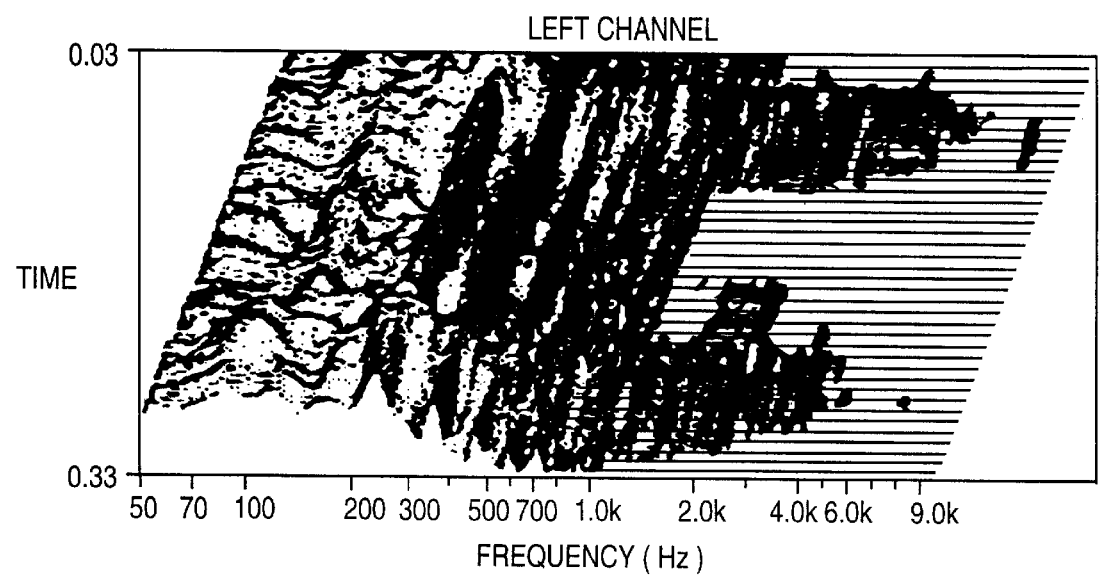
Figure 13C:
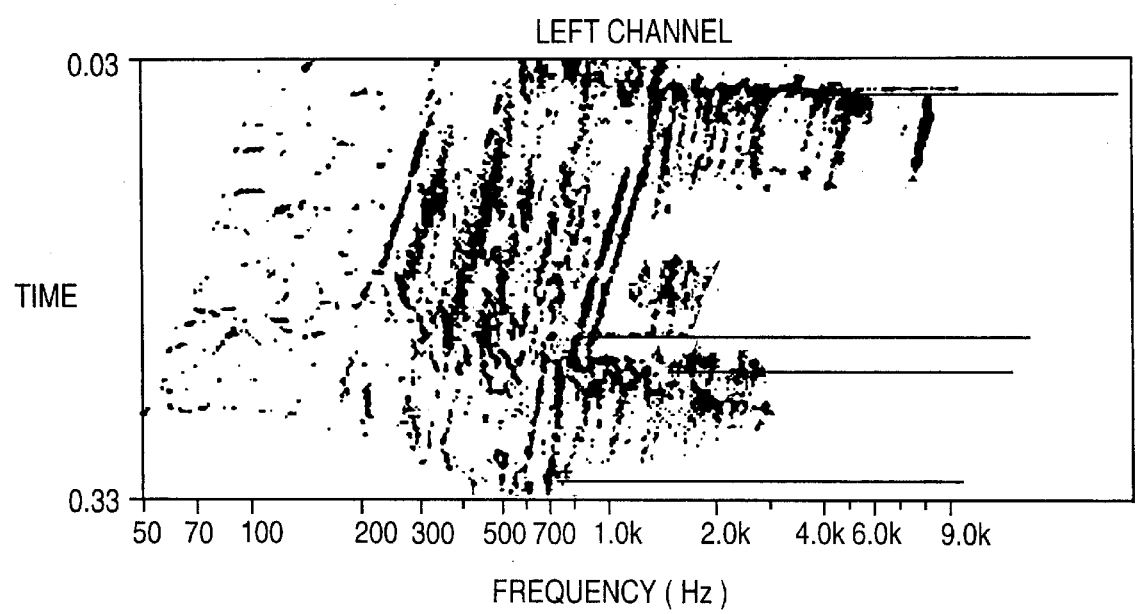
Figure 13D:
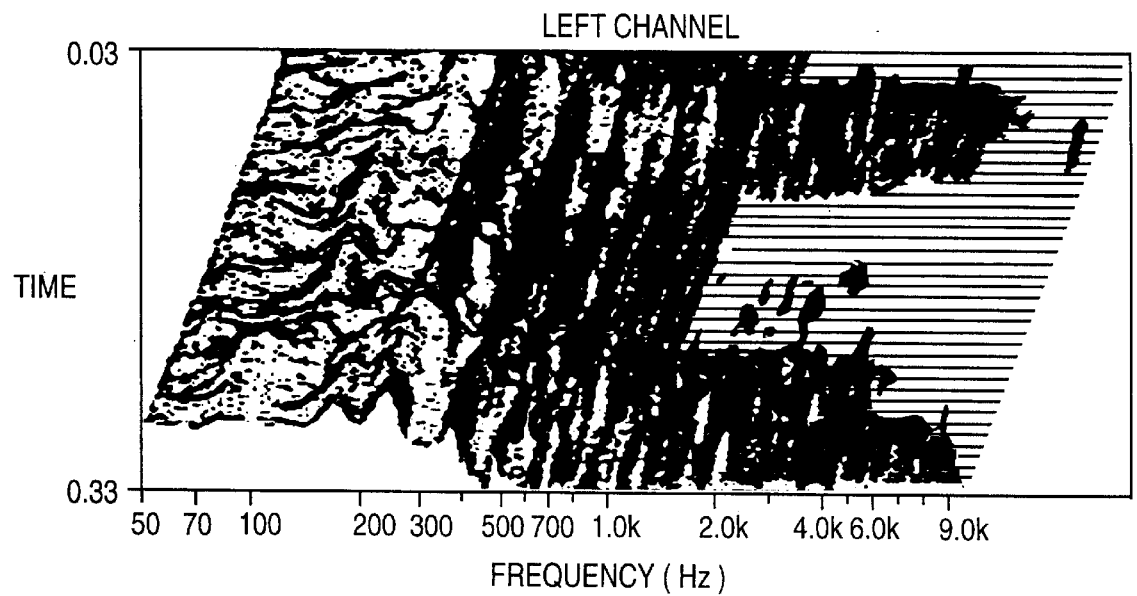
Figure 14A:
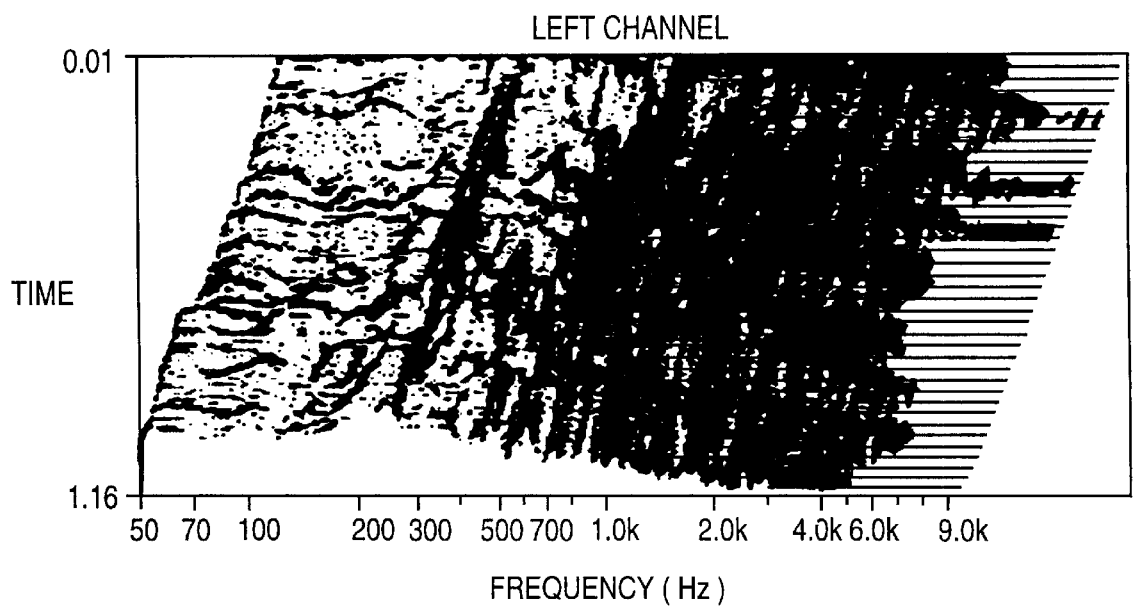
FIG. 14 depicts three dimensional signatures of trip step signatures of a like, properly operating reference unit to that referenced in FIG. 13.
Figure 14B:
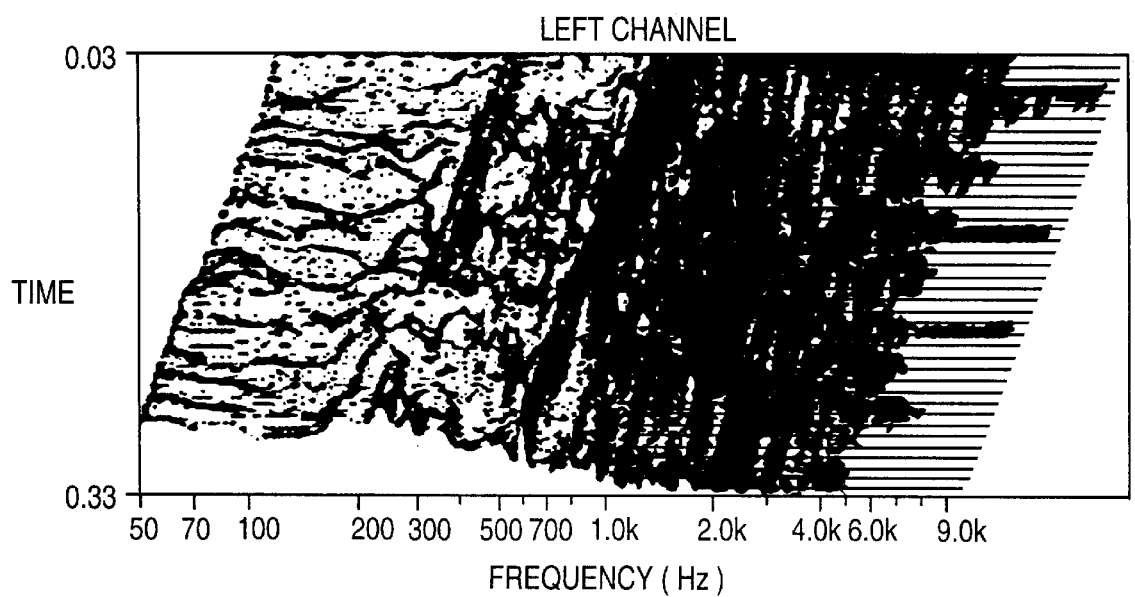
Figure 14C:
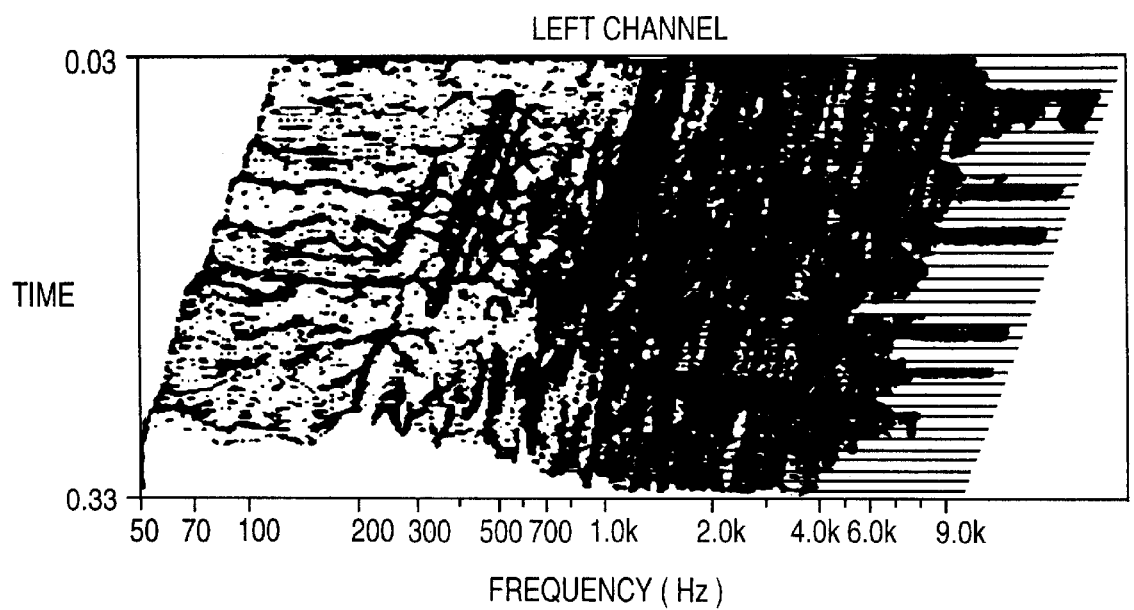
Figure 14D:
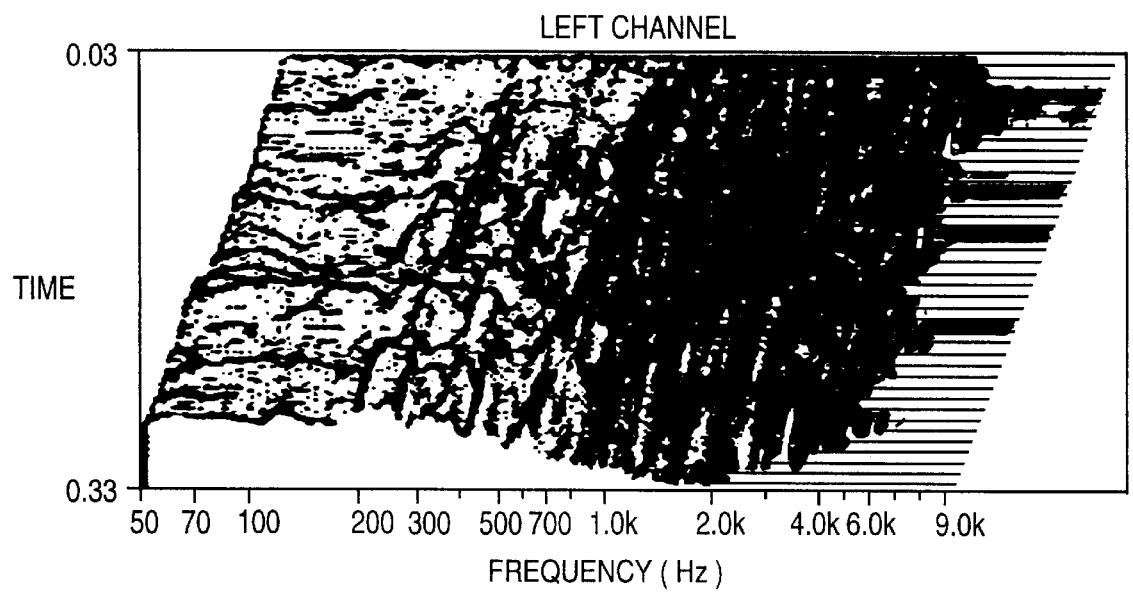

FIG. 9 shows the three display modes describe above with respect to a field test of the trip phase of an AC SDO 15500 breaker. FIG. 10 shows the same three display modes from the trip of a properly operating reference unit. The differences are apparent, and the particular unit the tests of which led to the images of FIG. 9 was found to require repairs upon disassembly and inspection. After repairs, the signatures of the repaired unit showed negligible differences from the reference signatures of FIG. 9 to confirm that the signatures of any two properly operating units of like make and model would substantially match.

FIGS. 11 and 12, respectively, show the pre-repairs recording from the close step of the same breaker and the close operation of a properly performing reference unit. Again, the differences are apparent from a simple, visual evaluation.

In the examples described above, the presence of "noise" at times, at frequencies, and/or in amplitudes which are not normally present in the signatures of properly operating equipment will indicate a malfunction. However, the converse is likewise true. Referring to FIGS. 13 and 14, respectively are shown the three dimensional signatures of the trip step of a defective LTC and the reference trip step signatures of a like, properly operating reference unit. The absence of sound in certain regions of the graphic depiction of the defective unit, as compared with the properly operating unit, is readily apparent. Once again, the need for repairs was clearly and reliably predicted through use of the present method.

Figure 15:
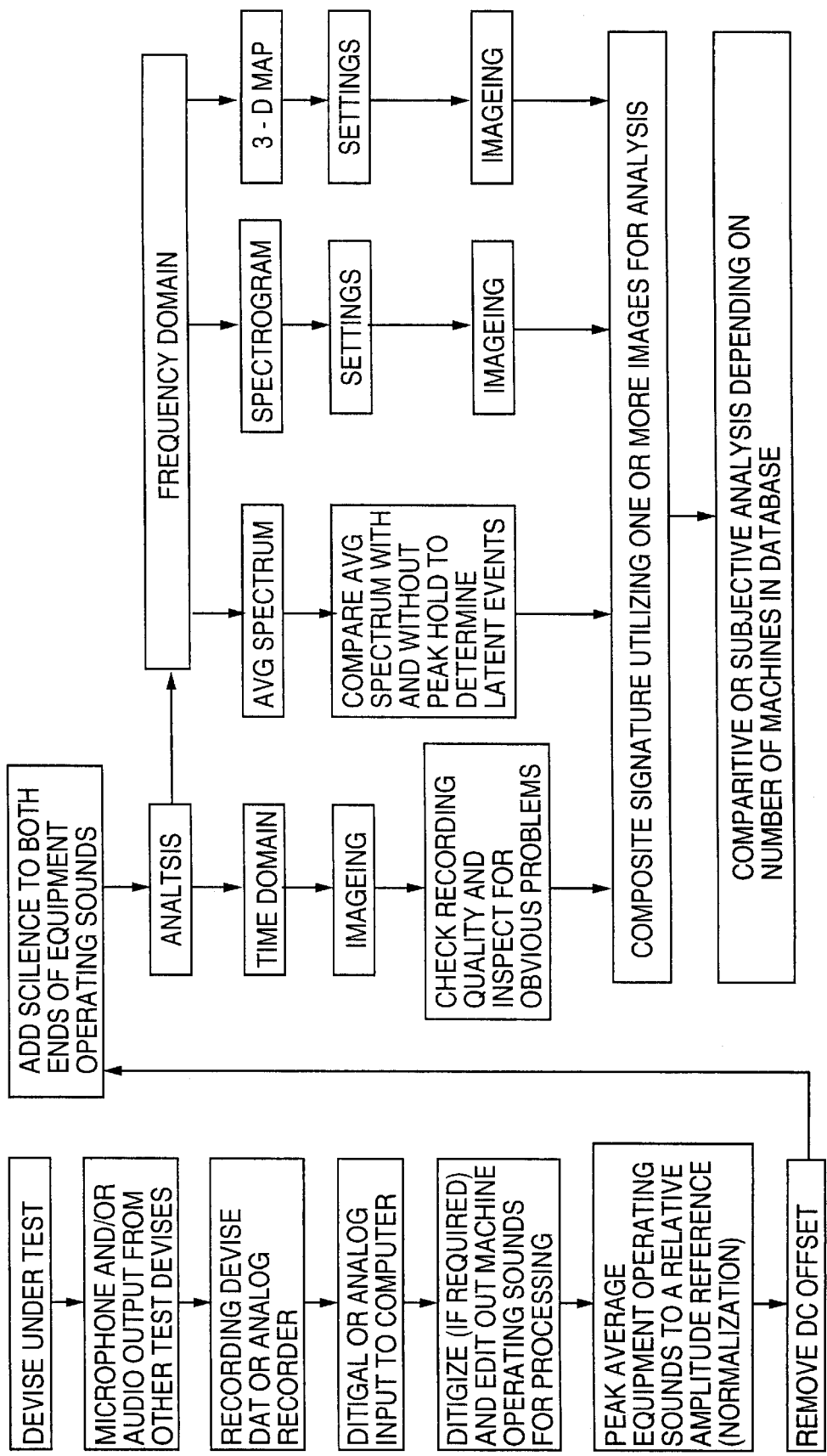
FIG. 15 is a flow chart depiction of the steps of a typical implementation of the present method.

A flow chart showing a typical utilization of the present method is depicted in FIG. 15.

It should be understood that, while the present discussion has centered on simple, human visual analysis and comparison of reference and test date from like equipment units, computer-based comparisons are well within the scope of the present invention. Neural networks and other forms of artificial intelligence in the computer realm can be implemented to "view" data and "recognize" variations between the data generated from reference and test units, The software can be configured to alert a user if such variations exceed certain prescribed thresholds. Use of such equipment and methods is merely another way of "viewing" and "comparing" the "graphical displays" generated through recording and processing as already described. Even though a visually perceptible display ("graphical display") may or not actually be generated for human viewing, the data which is represented by such a display is still represented to a computer whereby the same parameters are compared and differences are recognized. Therefore, "graphical display" as used in the claims is intended to encompass the substantive equivalent as is input into a computer for "viewing" by a computer.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A method for evaluating switching and breaker equipment for mechanical defects and improper operation comprising the steps of:

selecting microphone means and sound recording means and assembling said microphone means and said sound recording means for recording sound to recording media;

placing said microphone means in operative proximity to a first electrical distribution system breaker or switching device, said first electrical distribution system breaker or switching device being known to be in proper operating condition;

actuating said microphone means and said sound recording means to generate a first sound recording of said first electrical distribution system breaker or switching device in operation;

selecting data processing software and computer means and therewith generating a first graphical depiction of numerical values of measurable parameters of said first sound recording when read by said computer means and said data processing software;

placing said microphone means in operative proximity to a second electrical distribution system breaker or switching device;

actuating said microphone means and said sound recording means to generate a second sound recording of said second electrical distribution system breaker or switching device in operation;

using said data processing software and said computer means, generating a second graphical depiction of said numerical values of measurable parameters of said second sound recording when read by said computer means and said data processing software; and comparing said first graphical depiction with said second graphical depiction and identifying perceptible variations in depicted parameters there between as indications of variations in mechanical operations of said second electrical distribution system breaker or switching device when compared with said first electrical distribution system breaker or switching device.

* * * * *